US005534691A

United States Patent [19]
Holdaway et al.

[11] Patent Number: 5,534,691
[45] Date of Patent: Jul. 9, 1996

[54] SYSTEM FOR DETERMINING PUMPING MECHANISM POSITION WHILE LIMITING VOLUME OF FLUID PUMPED

[75] Inventors: Charles R. Holdaway, San Diego; Eric A. Warner, Vista, both of Calif.

[73] Assignee: IVAC Corporation, San Diego, Calif.

[21] Appl. No.: 304,582

[22] Filed: Sep. 12, 1994

[51] Int. Cl.⁶ ............................................. G01D 5/34
[52] U.S. Cl. ................................. 250/231.14; 604/67
[58] Field of Search .................. 250/231.13, 231.14, 250/231.18, 237 G; 356/395; 604/65, 67

[56] References Cited

U.S. PATENT DOCUMENTS

| | | | |
|---|---|---|---|
| 4,367,435 | 1/1983 | Bailey et al. | 318/313 |
| 4,601,700 | 7/1986 | Thompson et al. | 604/65 |
| 4,654,522 | 3/1987 | Gornick et al. | 250/231 SE |
| 4,736,187 | 4/1988 | Kibrick et al. | 250/231.14 |
| 4,863,425 | 9/1987 | Slate et al. | 604/67 |
| 4,912,389 | 3/1990 | Eguchi | 250/231.14 |
| 4,950,235 | 8/1990 | Slate et al. | 604/67 |
| 4,965,446 | 10/1990 | Vyse | 250/231.14 |
| 4,988,865 | 1/1991 | Schmidt et al. | 250/231.16 |
| 5,171,982 | 12/1992 | Kronenberg | 250/231.13 |

*Primary Examiner*—Edward P. Westin
*Assistant Examiner*—Steven L. Nichols
*Attorney, Agent, or Firm*—Fulwider Patton Lee & Utecht

[57] ABSTRACT

A drive member of a peristaltic pumping mechanism includes a disk that rotates with the drive member and has two transparent sectors and two opaque sectors alternating with the transparent sectors. As a stepper motor rotates the drive member to pump fluid, a single optical sensor senses the disk and provides signals indicative of whether a transparent sector or opaque sector is being detected. A processor counts the number of motor steps in the detected transparent or opaque sector and based on the number of counted steps in a type of sector detected or the number of steps counted when a state change to the other type of sector occurs, determines the motor position. In another aspect, the position disk is integrally formed as a single piece with the cams and cam shaft of a pumping mechanism.

14 Claims, 7 Drawing Sheets

| ANGLE | STEP # | PHOTO |
|---|---|---|
| 0 | 0 | 0 |
| 1.8 | 1 | 0 |
| 3.6 | 2 | 0 |
| 5.4 | 3 | 0 |
| 7.2 | 4 | 0 |
| 9 | 5 | 0 |
| 10.8 | 6 | 0 |
| 12.6 | 7 | 0 |
| 14.4 | 8 | 0 |
| 16.2 | 9 | 0 |
| 18 | 10 | 0 |
| 19.8 | 11 | 0 |
| 21.6 | 12 | 0 |
| 23.4 | 13 | 0 |
| 25.2 | 14 | 0 |
| 27 | 15 | 0 |
| 28.8 | 16 | 0 |
| 30.6 | 17 | 0 |
| 32.4 | 18 | 0 |
| 34.2 | 19 | 0 |
| 36 | 20 | 0 |
| 37.8 | 21 | 0 |
| 39.6 | 22 | 0 |
| 41.4 | 23 | 0 |
| 43.2 | 24 | 0 |
| 45 | 25 | 0 |
| 46.8 | 26 | 0 |
| 48.6 | 27 | 0 |
| 50.4 | 28 | 0 |
| 52.2 | 29 | 0 |
| 54 | 30 | 0 |
| 55.8 | 31 | 0 |
| 57.6 | 32 | 0 |
| 59.4 | 33 | 0 |
| 61.2 | 34 | 0 |
| 63 | 35 | 0 |
| 64.8 | 36 | 0 |
| 66.6 | 37 | 0 |
| 68.4 | 38 | 0 |
| 70.2 | 39 | 0 |
| 72 | 40 | 0 |
| 73.8 | 41 | 0 |
| 75.6 | 42 | 0 |
| 77.4 | 43 | 0 |
| 79.2 | 44 | 0 |
| 81 | 45 | 0 |
| 82.8 | 46 | 0 |
| 84.6 | 47 | 1 |
| 86.4 | 48 | 1 |
| 88.2 | 49 | 1 |
| 90 | 50 | 1 |
| 91.8 | 51 | 1 |
| 93.6 | 52 | 1 |
| 95.4 | 53 | 1 |
| 97.2 | 54 | 1 |
| 99 | 55 | 1 |
| 100.8 | 56 | 1 |
| 102.6 | 57 | 1 |
| 104.4 | 58 | 1 |
| 106.2 | 59 | 1 |
| 108 | 60 | 1 |
| 109.8 | 61 | 1 |
| 111.6 | 62 | 1 |
| 113.4 | 63 | 1 |
| 115.2 | 64 | 1 |
| 117 | 65 | 1 |
| 118.8 | 66 | 1 |
| 120.6 | 67 | 1 |
| 122.4 | 68 | 0 |
| 124.2 | 69 | 0 |
| 126 | 70 | 0 |
| 127.8 | 71 | 0 |
| 129.6 | 72 | 0 |
| 131.4 | 73 | 0 |
| 133.2 | 74 | 0 |
| 135 | 75 | 0 |
| 136.8 | 76 | 0 |
| 138.6 | 77 | 0 |
| 140.4 | 78 | 0 |
| 142.2 | 79 | 0 |
| 144 | 80 | 0 |
| 145.8 | 81 | 0 |
| 147.6 | 82 | 0 |
| 149.4 | 83 | 0 |
| 151.2 | 84 | 0 |
| 153 | 85 | 0 |
| 154.8 | 86 | 0 |
| 156.6 | 87 | 0 |
| 158.4 | 88 | 0 |
| 160.2 | 89 | 0 |
| 162 | 90 | 0 |
| 163.8 | 91 | 0 |
| 165.6 | 92 | 0 |

FIG. 3(A)

| ANGLE | STEP # | PHOTO |
|---|---|---|
| 167.4 | 93 | 1 |
| 169.2 | 94 | 1 |
| 171 | 95 | 1 |
| 172.8 | 96 | 1 |
| 174.6 | 97 | 1 |
| 176.4 | 98 | 1 |
| 178.2 | 99 | 1 |
| 180 | 100 | 1 |
| 181.8 | 101 | 1 |
| 183.6 | 102 | 1 |
| 185.4 | 103 | 1 |
| 187.2 | 104 | 1 |
| 189 | 105 | 1 |
| 190.8 | 106 | 1 |
| 192.6 | 107 | 1 |
| 194.4 | 108 | 1 |
| 196.2 | 109 | 1 |
| 198 | 110 | 1 |
| 199.8 | 111 | 1 |
| 201.6 | 112 | 1 |
| 203.4 | 113 | 1 |
| 205.2 | 114 | 1 |
| 207 | 115 | 1 |
| 208.8 | 116 | 1 |
| 210.6 | 117 | 1 |
| 212.4 | 118 | 1 |
| 214.2 | 119 | 1 |
| 216 | 120 | 1 |
| 217.8 | 121 | 1 |
| 219.6 | 122 | 1 |
| 221.4 | 123 | 1 |
| 223.2 | 124 | 1 |
| 225 | 125 | 1 |
| 226.8 | 126 | 1 |
| 228.6 | 127 | 1 |
| 230.4 | 128 | 1 |
| 232.2 | 129 | 1 |
| 234 | 130 | 1 |
| 235.8 | 131 | 1 |
| 237.6 | 132 | 1 |
| 239.4 | 133 | 1 |
| 241.2 | 134 | 1 |
| 243 | 135 | 1 |
| 244.8 | 136 | 1 |
| 246.6 | 137 | 1 |
| 248.4 | 138 | 1 |
| 250.2 | 139 | 1 |
| 252 | 140 | 1 |
| 253.8 | 141 | 1 |
| 255.6 | 142 | 1 |
| 257.4 | 143 | 1 |
| 259.2 | 144 | 1 |
| 261 | 145 | 1 |
| 262.8 | 146 | 1 |
| 264.6 | 147 | 1 |
| 266.4 | 148 | 1 |
| 268.2 | 149 | 1 |
| 270 | 150 | 1 |
| 271.8 | 151 | 1 |
| 273.6 | 152 | 1 |
| 275.4 | 153 | 1 |
| 277.2 | 154 | 1 |
| 279 | 155 | 1 |
| 280.8 | 156 | 1 |
| 282.6 | 157 | 1 |
| 284.4 | 158 | 1 |
| 286.2 | 159 | 1 |
| 288 | 160 | 1 |
| 289.8 | 161 | 1 |
| 291.6 | 162 | 1 |
| 293.4 | 163 | 1 |
| 295.2 | 164 | 1 |
| 297 | 165 | 1 |
| 298.8 | 166 | 1 |
| 300.6 | 167 | 1 |
| 302.4 | 168 | 1 |
| 304.2 | 169 | 1 |
| 306 | 170 | 1 |
| 307.8 | 171 | 1 |
| 309.6 | 172 | 1 |
| 311.4 | 173 | 1 |
| 313.2 | 174 | 1 |
| 315 | 175 | 1 |
| 316.8 | 176 | 1 |
| 318.6 | 177 | 1 |
| 320.4 | 178 | 1 |
| 322.2 | 179 | 1 |
| 324 | 180 | 1 |
| 325.8 | 181 | 1 |
| 327.6 | 182 | 1 |
| 329.4 | 183 | 1 |
| 331.2 | 184 | 1 |
| 333 | 185 | 1 |
| 334.8 | 186 | 1 |
| 336.6 | 187 | 1 |
| 338.4 | 188 | 1 |
| 340.2 | 189 | 1 |
| 342 | 190 | 1 |
| 343.8 | 191 | 1 |
| 345.6 | 192 | 1 |
| 347.4 | 193 | 1 |
| 349.2 | 194 | 1 |
| 351 | 195 | 1 |
| 352.8 | 196 | 1 |
| 354.6 | 197 | 1 |
| 356.4 | 198 | 1 |
| 358.2 | 199 | 1 |

FIG. 3(B)

SYSTEM FOR DETERMINING PUMPING MECHANISM POSITION WHILE LIMITING VOLUME OF FLUID PUMPED

BACKGROUND

The present invention relates generally to position detection and more particularly, to a system and method for determining the position of a drive member using a positioning disk adapted to be rotated with that drive member.

For the more precise infusion of parenteral fluids into a patient, infusion pumps have been developed. These pumps have allowed greater control over the infusion rate and have been beneficial in the administration of parenteral fluids in many ways. However, there is a continuing desire for improvement in the accuracy and precision of these pumps over a wide range of flow rates.

One type of infusion pump is a linear peristaltic pump. In this pump, a drive motor rotates a shaft to cause cams to move pinching fingers into and out of contact with a fluid conduit causing the sequential occlusion in a wave-like motion of the conduit. This sequential occlusion forces the parenteral fluid from a reservoir into the patient at a programmed flow rate. The cams are disposed along the camshaft so that adjacent cam lobes project at different angular positions relative to the camshaft. The occluding fingers follow the respective cam lobes as the motor rotates. The drive motor is typically a stepper motor having a selected number of motor steps per complete rotation; for example, two-hundred steps. In general, the stepper motor rotates in a sequential, incremental, step-by-step manner over a complete rotation, the complete rotation defining a pump cycle.

Each incremental movement or step of the motor causes a corresponding incremental movement of the cams and fingers that results in a discrete volume of fluid being pumped. This discrete volume may be referred to as a "step volume". Because of the various mechanical parts involved, their inter-relationships and the linear configuration of the pumping mechanism, an inherent characteristic of linear peristaltic pumps is that step volumes deviate from each other. Furthermore, the mechanical configuration of the linear peristaltic pump results in reverse flow in the flexible conduit at some point or points in the pumping cycle and the step volumes at those points is actually negative.

The particular volumetric quantity pumped by each movement of a pumping mechanism can be measured by means such as gravimetric measurement and can then be stored for later reference. A stepper motor provides a convenient reference for pump mechanism position and movement in that defined increments of movement or "steps" exist with stepper motors. Because the stepper motor is typically rigidly mounted to the camshaft, a step of the motor always results in a movement increment of the camshaft, the cams, and the pumping fingers. Thus, determining a position of the camshaft enables one to determine the position of the motor driving the camshaft. In cases where step volumes are considered in the control of the pump, the position of the drive member must be known so that the step volume can be considered. Such an application may exist where flow uniformity is to be increased. Therefore, more precise motor position information is required.

Upon start up of an infusion pump the drive member position is typically unknown by the pump processor. Because of this condition, a pump that considers step volumes to increase flow uniformity cannot begin its control of the motor position for this purpose and must let the pump run until the position can be determined. The processor must first determine at which step the motor is located. It is therefore desirable for the processor to be able to determine the motor drive member position quickly so that the quantity of fluid pumped before that position is determined is not excessive.

In one previous system to determine motor position, a positioning disk is attached to the drive motor shaft and has a plurality of concentric circular tracks of different radii, each track formed with openings of different angular widths. Associated with each track is an optical sensor, such as a light emitting diode coupled with a photo-detector, to detect the angular openings. The openings are configured on the plurality of tracks to correspond to predetermined binary codes representative of a particular motor position. The openings are sensed during rotation of the encoder disk and the particular motor position determined. However, this system incorporates multiple sensors with their attendant multiple output signals resulting in increased complexity and expense and requiring more complex software to decipher the many data inputs to derive a particular motor position.

One less complicated system utilizes a single flag-type indicator positioned on the motor drive shaft for indicating position. Some linear peristaltic systems use this flag to indicate the end of the normal pump cycle and the beginning of the speed-up cycle. While hardware and software costs are reduced with such a system, it can take almost one complete rotation of the motor to determine the drive member position when the motor start up position is just after the flag. Allowing this amount of time and movement to pass before being able to determine the drive member position can be undesirable especially where negative flow steps are involved.

Another consideration in using position disks or flags is the accuracy required in physically mounting them on the cam shaft. Likewise, where multiple cams are used, they must be accurately positioned on the camshaft in relation to each other and to the position disk. Where all of these parts are separate, each must be individually aligned resulting in increased complexity and expense.

Hence, those skilled in the art have found it desirable to provide more precise information pertaining to the position of a drive member while at the same time, lowering hardware and software costs. The system should be capable of quickly and efficiently determining the drive member rotational position without excessive pumping before that position is determined and without the use of relatively expensive, complex hardware or software. It has also been recognized as desirable to provide an infusion pumping system that alleviates the necessity of individually aligning multiple pumping and position detection. components. The present invention fulfills these needs and others.

SUMMARY OF THE INVENTION

The present invention provides a system for determining the position of a drive member that moves in sequential increments over a complete rotation. Drive member position is determined by sensing a plurality of position markers disposed on a disk that rotates in increments with the drive member.

Briefly and in general terms, a processor controls a motor to move the drive member in movement increments through a motor cycle. A disk moves with the drive member and includes a plurality of position markers disposed thereon. A sensor senses the markers as the disk rotates with the drive member producing a position signal at each movement increment corresponding to which marker is being sensed. The processor counts the number of movement increments turned during the sensing of a marker and between a sensed changed in marker types. The processor calculates the position of the drive member based on the number of movement increments counted in a marker or markers and the number of increments before or after a change in the marker type sensed.

In one aspect of the invention, the position markers of the disk comprise transparent and opaque radial sectors of different angular sizes in an alternating transparent and opaque configuration, and the sensor comprises an optical type detector used to sense a light beam that is broken by the passing of an opaque sector during disk rotation.

In a more particular aspect of the invention, the position markers of the disk comprise two transparent sectors, each having a different angular size, and two opaque sectors each having a different angular size. The angular sizes of the sectors are selected to correspond to a different plurality of movement increments so that a system processor in counting the number of movement increments before a sector change occurs can determine the motor drive member position in much less than one complete motor rotation.

In another aspect of the invention, the plurality of transparent sectors may comprise open apertures and only a single optical sensor is used.

In a further aspect of the invention, the position disk is formed integrally and as a single piece with the cam shaft and cams to form the drive member of a peristaltic pumping mechanism that is rotated by a stepper motor to pump fluid through a conduit. In another aspect, the drive member is formed of a plastic with the break lines of the mold placed on non-critical surfaces of the cams.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 3 is a tabular representation of drive member incremental positions corresponding to the predetermined location of the transparent and opaque markers of the positioning disk and the respective angular position thereof;

DETAILED DESCRIPTION OF THE PREFERRED EMBODIMENTS

Figure 1:
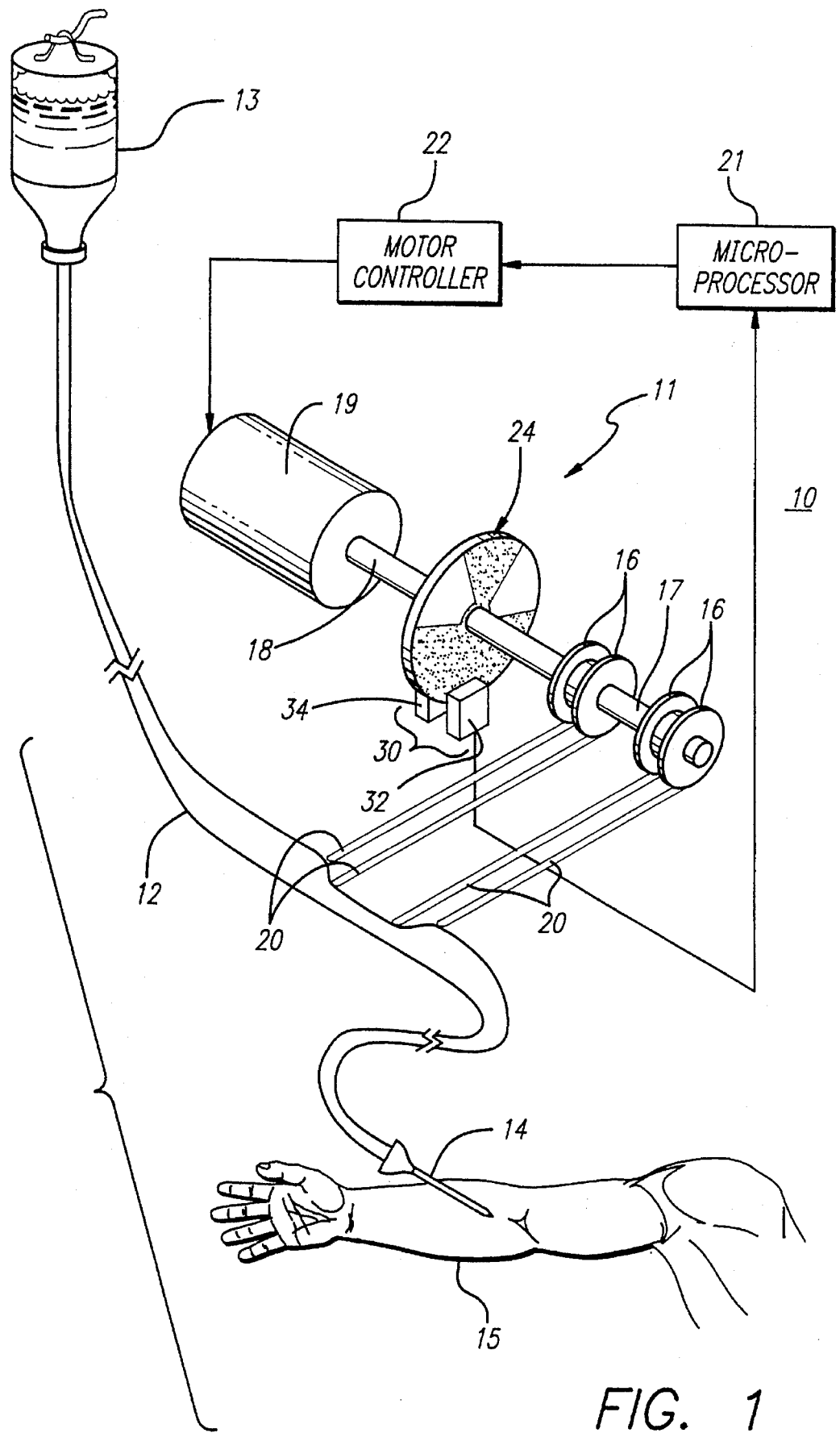
FIG. 1 is a schematic illustration of a peristaltic fluid delivery system including a motor controlled to move in sequential movement increments coupled to a pump shaft attached to a positioning disk in accordance with an aspect of the invention.

In the following description, like reference numerals will be used to refer to like or corresponding elements in the different figures of the drawings. Referring now to the drawings and particularly to FIG. 1, there is shown a schematic illustration of a parenteral fluid administration system 10 embodying features of the invention. In this embodiment, the fluid administration system comprises a linear peristaltic pump 11 to exert pressure in a peristaltic wave-like motion against a fluid administration set conduit 12 to force fluid from a fluid reservoir 13 through a cannula 14 intravenously to a patient 15. The peristaltic pump 11 includes a plurality of cams 16 mounted to a camshaft 17, the camshaft being coupled to the drive member 18 of a drive motor 19. The cams are mounted, for instance, by press-fitting on the camshaft 17 so that adjacent cam lobes project at different angular positions relative to the camshaft. As shown in this embodiment, the drive member 18 is directly coupled to the camshaft 17 although in other embodiments, a different arrangement is possible. Each cam is respectively followed by a pumping finger 20, each finger sequentially occluding an adjacent portion of the tubing 12 to drive fluid through the tubing in response to the rotation of the camshaft and camming motion of the cams.

In the preferred embodiment, the drive motor 19 is a stepper motor that moves through a complete rotation or pump cycle in sequential movement increments or steps. The fluid delivery system 10 has a microprocessor 21 that provides control signals to a motor controller 22 to advance the stepper motor 19 through the sequential steps thereby driving the camshaft, cams, and fingers. Because of the mechanical configuration of the pumping mechanism including the inter-linking of the peristaltic pump 11 components, each step that the stepper motor moves causes a discrete corresponding movement of the cams 16 and fingers 20 and an interaction with the tubing 12 by the respective fingers. Therefore, as the microprocessor 21 controls the motor 19 to move a step, a corresponding step volume is pumped through the tubing.

In the preferred embodiment, a position location disk 24 is adapted to move with the motor drive member 18. In this case, the disk has a hub with an axial bore therethrough and is mounted by press-fitting onto the camshaft 17 between the cams 16 and the motor 19. Because of the direct connection with the motor drive member 18, each position of the disk 24 corresponds to a particular position of the drive member 18 and the motor 19. The position location disk 24 has a plurality of markers comprising alternating transparent sectors and opaque sectors. The markers of the position disk 24 are sensed by a single optical sensor 30 located adjacent thereto. The sensor comprises a photo transistor light detector 32 and a light source 34, such as a light emitting diode (LED), with the light source and photo detector being located in a spaced-apart, confronting relationship on opposite sides of the disk. The photo detector 32 and light source 34 are positioned so that a light beam directed toward the rotating disk is sensed by the photo detector when the transparent sectors of the disk are positioned between the optical sensor device and the light beam is interrupted when the opaque sectors are positioned between the optical sensor device.

Figure 2:
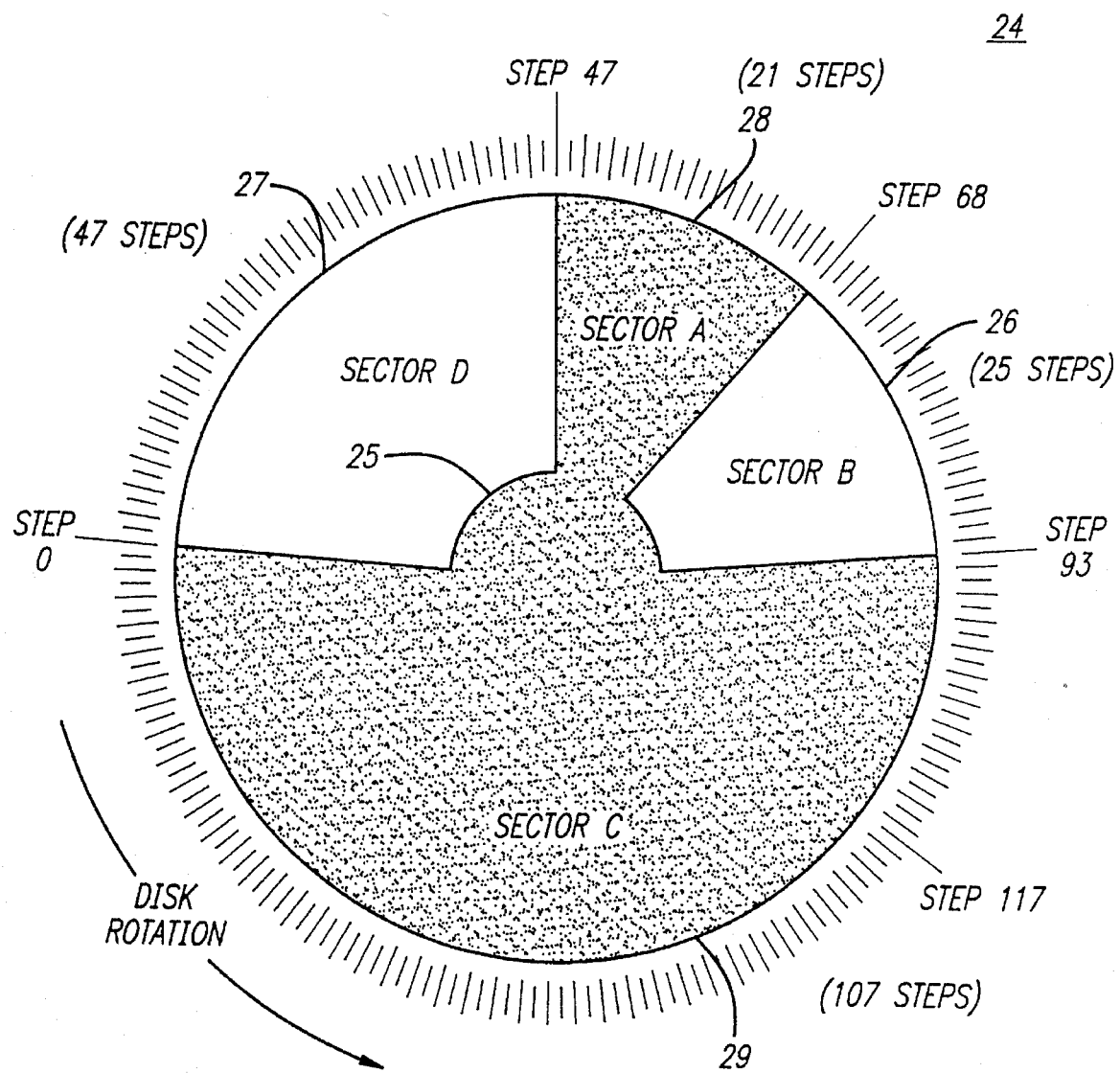
FIG. 2 is an enlarged view of the positioning disk shown in FIG. 1 having a plurality of alternating transparent and opaque markers of selected sizes in accordance with an aspect of the invention.

Referring now to FIG. 2, the position disk 24 is shown with more particularity and has two opaque sectors, Sector A 28 and Sector C 29 and two transparent sectors, Sector B 26 and Sector D 27. The sectors alternate between transparent and opaque. In the embodiment shown, the opaque sectors comprise solid disk sections while the transparent sectors are formed by cutting away the disk material. The disk may be composed of an opaque Teflon-filled polycarbonate plastic. Alternatively, the disk 24 may be formed of slotted black anodized aluminum or brass. In another embodiment, the disk may be formed as a solid plastic disk having opaque and transparent portions to define the respective sectors.

The stepper motor 19 has two-hundred equally spaced motor steps in each full rotation. As the stepper motor moves sequentially in a step-by-step manner, the position disk correspondingly rotates in step-by-step angular movement increments past the sensor 30. These step increments are shown by the tick marks outside the periphery of the disk 24 in FIG. 2. The sensitivity of the photo-detector 32 (FIG. 1) is such that it can sense whether a transition has been made from an opaque sector to a transparent sector and vice-versa upon a single step of the stepper motor. Therefore, the markers in this embodiment are the opaque and transparent sectors and inherently, their transitions.

In general, a marker indicates a change in state, the disk of the preferred embodiment having two states, light and dark. Because the markers have width, four state changes occur over a complete rotation of the disk; two light-to-dark transitions and two dark-to-light transitions. In other configurations, a marker may comprise a different type of indicator such as a magnetic strip whereby a magnetic sensor would sense whether the magnetic strip has passed indicating a change in state. Such a magnetic sensor may be a variable reluctance sensor or Hall effect sensor.

In FIG. 3, a tabular representation of the locations of the positioning markers disposed on the position disk are shown corresponding to sequential step positions and their respective angular positions. In the columns labeled "Step" 36, sequential motor steps numbered consecutively from zero to one hundred and ninety nine are presented and comprise a complete motor rotation. The tick marks on the disk 24 shown in FIG. 2 indicate the motor steps listed. Corresponding sequential angular step positions are listed in the "Angle" columns 37. Each angular increment in this embodiment is 1.8 degrees. The table also illustrates in the columns labeled "Photo" 38 the logical value of each step. In this embodiment, a logical value of "1" indicates an opaque or dark sector while a logical value of "0" indicates a transparent or light sector. One can ascertain the location and size of the position markers on the disk and whether a particular sector is transparent or opaque. As shown in both FIGS. 2 and 3, the first dark Sector A 28 has twenty-one steps and the second dark Sector C 29 has one-hundred and seven steps. The first light Sector B 26 has twenty-five steps and the second light Sector D 27 has forty-seven steps.

Sector A=21 steps (dark)
Sector B=25 steps (light)
Sector C=107 steps (dark)
Sector D=47 steps (light)

By virtue of the number of transparent and opaque sectors, their sizes and their placements, the system can determine the position of the disk and motor within a limited number of disk movement increments by sensing the transitions from transparent to opaque sectors, and vice versa, and thereafter counting the number of steps taken in conjunction with state changes.

During the manufacture of the position disk 24, it may be difficult to obtain a precise edge between the transparent and opaque sectors relative to the small motor steps. Additionally the resolution of the optical detector may result in step uncertainty. Therefore, the embodiment described here takes into consideration manufacturing tolerances as well as optical detector resolution. In this case, the system allows for uncertainty or error tolerance of plus or minus two steps.

Figure 4:
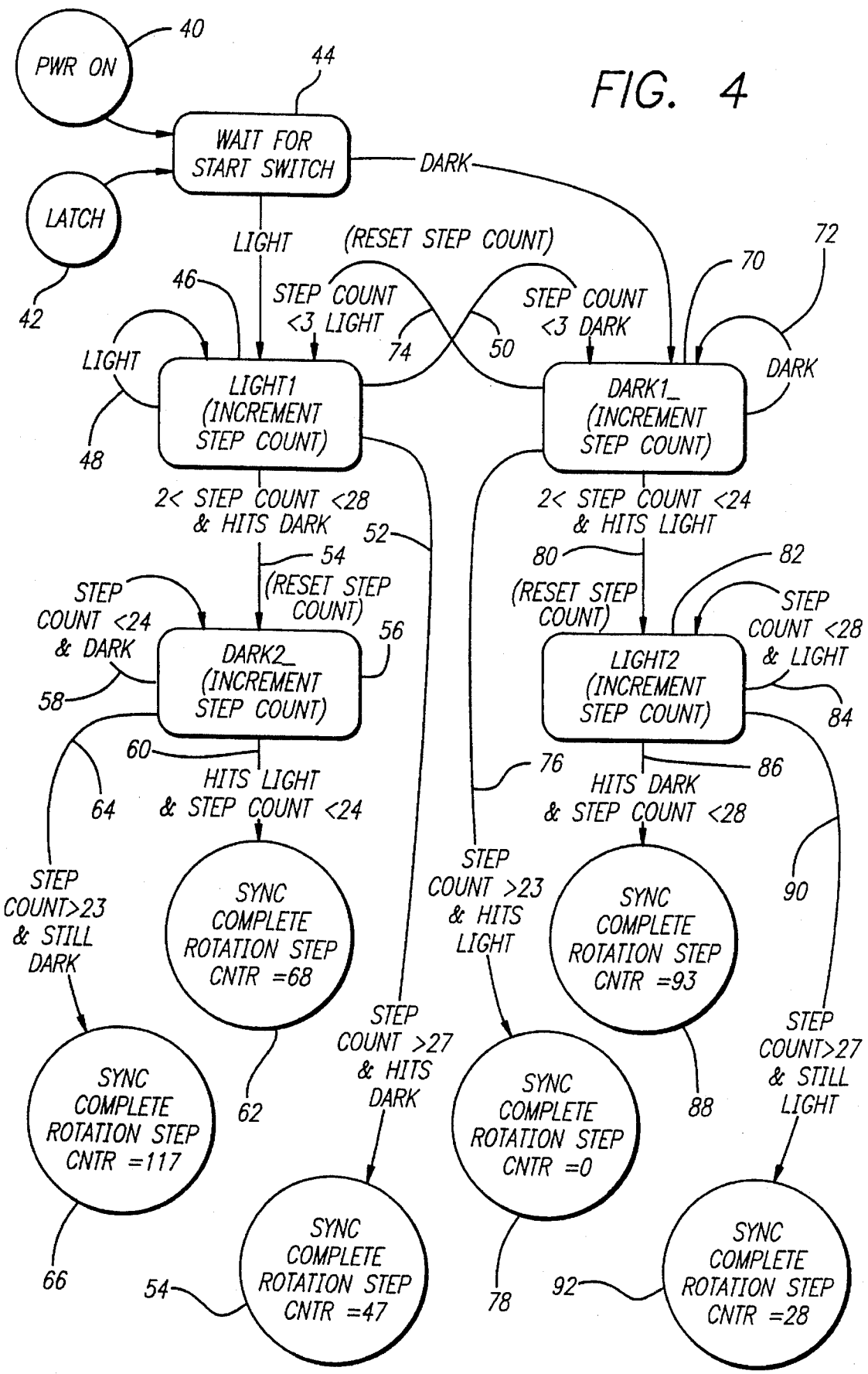
FIG. 4 is a state chart showing process steps to determine drive member position derived from sensing the transparent and opaque markers as the positioning disk rotates in accordance with the invention.

Referring now to FIG. 4, an example of operation of the system is presented. The operator actuates the system power 40 to energize the pumping system. A latch 42 is interlocked with a start switch 44 to prevent the start switch from being energized until proper installation of the fluid conduit into the pumping system and other events have first occurred. Once the latch has been set 42 and the start switch has been actuated 44, the microprocessor 21 (FIG. 1) controls the motor 16 to turn in a sequential step-by-step manner. As described above, the motor and drive member 18 may be at an unknown position at pump start up. The microprocessor 21 causes step-by-step movement of the motor and drive member and monitors the output of the optical sensor 30 at each of those steps. The optical sensor 30 outputs a signal indicative of whether it is presenfiy sensing a transparent or opaque sector and by monitoring its state changes and the number of steps taken by the drive member after or before state changes, the processor can rapidly determine the motor position.

When the microprocessor 21 initiates the first step of rotation of the motor, it has been found that such stepper motors may initially reverse direction in that first step from that which was intended. Therefore, it is possible for the detector to detect a state change in the reverse direction. In recognition of this phenomena, if the optical detector detects a state change within three steps of rotation, a count reset feature has been incorporated in the system to overcome any possibilities of initial reverse motor rotation.

Figure 5:
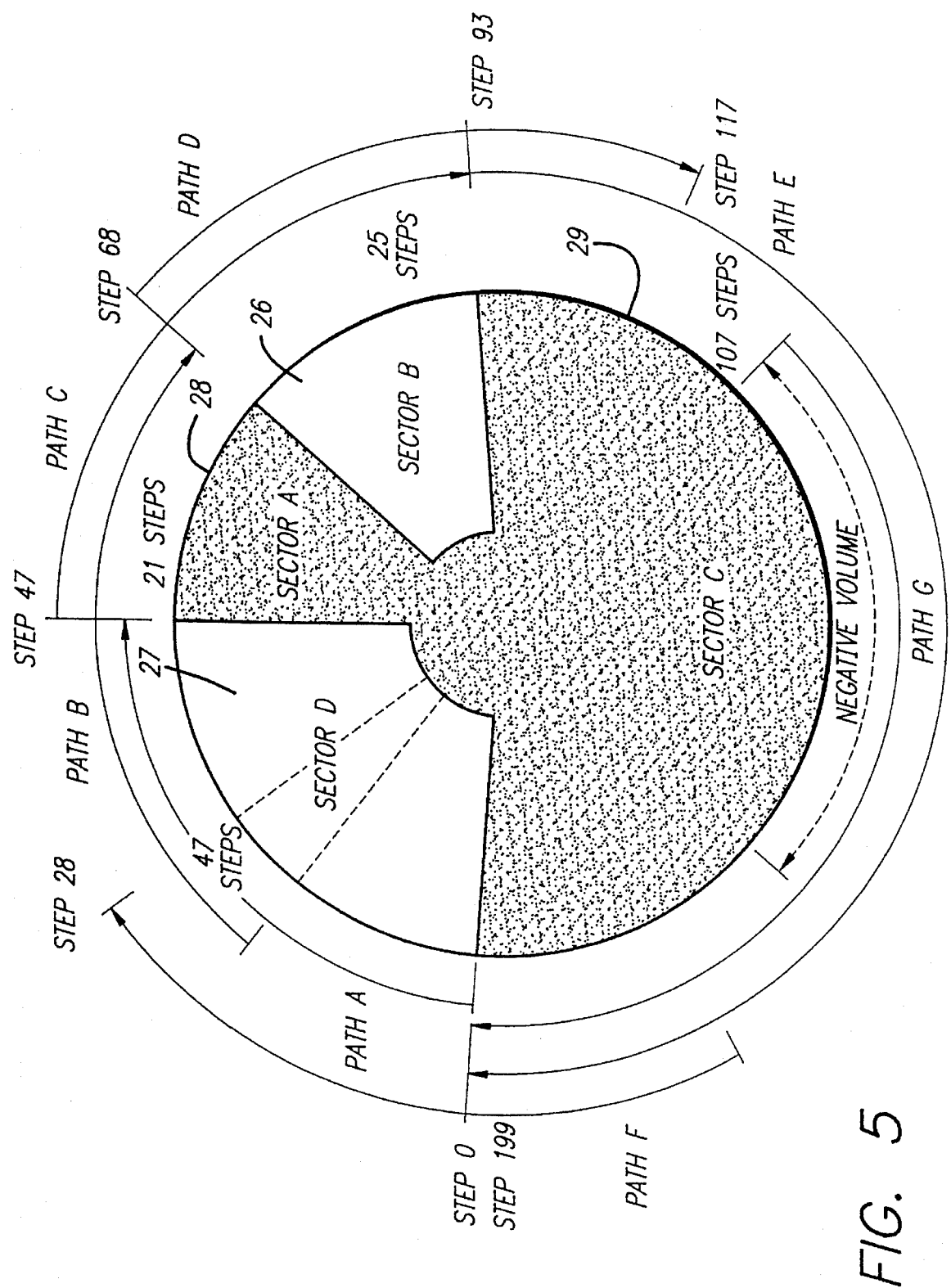
FIG. 5 is a graph of the disk of FIG. 2 with flow paths indicated to graphically demonstrate the synchronizing of the disk position with motor step position.

Referring now to both FIGS. 4 and 5, if at start up the optical sensor first detects a light sector 46 (LIGHT1), the microprocessor controls the motor to step again and begins counting the number of motor steps taken 48. If the sensor detects an opaque sector in less than three steps 50, the microprocessor resets the step count, to overcome initial motor rotation fluctuation as described above, and thereafter initiates a first dark count 70 (DARK1), the operation of which will be described below. If the number of consecutive "light" steps counted is greater than twenty-seven 52, (includes the two-step compensation for uncertainty) when an opaque sector is encountered, the microprocessor knows that the sensor has detected Sector D 27 and the processor assigns 54 motor step number forty-seven to the transition position of light to dark. The position of the drive member has therefore been determined and "synchronization" has occurred. This rapid position determination has occurred in this case because the first transparent Sector B 26, has only twenty-five steps. Thus, if the drive member has turned more than twenty-five steps, plus two steps to allow for sector edge tolerance uncertainty, without a state change to an opaque sector, the drive member is necessarily in the second transparent Sector D 27. Waiting until the state changes to "dark" informs the microprocessor of the exact position of the drive member.

If the number of consecutive "light" steps counted 48 before a "dark" sector is encountered is greater than two but less than twenty-eight 54, the microprocessor 21 resets the step count and initiates a second dark count 56 (DARK2) as it is unable to tell which transparent sector the drive member was in when the change occurred. If the number of dark signals counted is less than twenty-four when a transparent sector is detected 60, the microprocessor determines that the drive member is now at step position number sixty-eight (at the sector change). The drive member position is now known and is synchronized. The microprocessor was able to reach this conclusion because the first opaque sector 28 has only twenty-one steps in it while the second opaque sector 29 has one hundred and seven steps. The processor knew when entry into the dark sectors occurred, thus, a sector change in twenty-one steps, plus two steps to allow for sector edge tolerance uncertainty, positively indicates that the optical sensor was in the first opaque Sector A 28.

If after transitioning from light to dark, the number of dark steps counted is greater than twenty-three 64, the processor then knows that the sensor is in the second opaque Sector C 29. Because the processor knew when the sensor began detecting the dark sector, it does not need to wait for another sector change but instead can assign 66 the position to step number one hundred and seventeen. The microprocessor was able to reach this conclusion because the first opaque Sector A 28 has only twenty-one steps in it; thus, exceeding that amount, plus two steps to allow for sector edge tolerance uncertainty, means that the sensor is in the second opaque Sector C 29.

If, in the alternative, the first sector detected by the sensor 30 at start up 44 is a dark sector, the microprocessor 21 initiates a first dark count (DARK1) 70 and begins counting the consecutive number of "dark" steps 72. If the number of dark steps is less than three 74 before a transparent sector is detected, the microprocessor resets the step count, and thereafter initiates the first light count "LIGHT1" 46 and begins the routine described above.

If the number of dark steps counted 72 is greater than twenty-one 76, plus two steps to allow for sector edge tolerance uncertainty, when a transparent sector is sensed, the microprocessor knows that the sensor was in Sector C 29 and assigns step position number zero to the drive member position at the state change from dark to light. This is because only opaque Sector C 29 has a size greater than twenty-one steps. However, the processor must wait until a state change occurs to precisely determine the position.

If the number of steps of consecutive "dark" signals generated 72 is greater than two but less than twenty two, plus two steps to allow for sector edge tolerance uncertainty, when a transparent sector is detected 80, the microprocessor 21 does not know which dark sector the sensor was detecting and initiates the second light count 82 (LIGHT2) and begins counting the consecutive number of "light" steps. If the number of light steps counted before a dark signal is generated is less than twenty six 86, plus two steps to allow for sector edge tolerance uncertainty, the microprocessor assigns step number ninety three to that step position because the microprocessor knows it was in Sector B 26.

If the number of "light" steps counted reaches twenty six 90, plus two steps to allow for sector edge tolerance uncertainty, before a "dark" signal is generated, the microprocessor assigns step number twenty eight to that particular step position 92. This is because only the second transparent Sector D 27 has a size greater than twenty-five steps. By sensing a number of light steps greater than twenty-five (the size of Sector B), plus two steps to allow for sector tolerance uncertainty, the microprocessor knows that the drive member must be in Sector D.

The sector sizes and locations have been selected to result in rapid position determination so that flow before determination is not excessive and is not negative. FIG. 5 presents some examples of the rapid synchronization times with worst case start-up positions. In Path A, the motor starts up with the sensor detecting Sector D just past Sector C. As described above, the system will be able to set the position of the motor at step forty seven when the sector change from light to dark is detected because the sensor will have detected more than the twenty-five steps of light, plus two steps to allow for sector edge tolerance uncertainty, that are in Sector B.

The motor starts up in Path B in Sector D but with fewer than twenty-five steps of light, plus two steps to allow for sector tolerance uncertainty, so that the processor does not know which light sector the sensor detected. However, upon changing state from light to dark, counting twenty-one steps, and changing state from dark to light, the processor can determine that the detector is now at step sixty eight because the other dark sector has far more steps.

In Path C, the sensor starts in Sector A just after Sector D and counts twenty-one steps of dark before a state change to light. The processor is therefore unable to determine which dark sector the startup occurred in. However, after a state change from light to dark twenty-five steps later, the processor can determine that the position is now step ninety three as Sector D has many more steps of light.

Path D begins in Sector B just after Sector A. Because there are only twenty-five steps in Sector B, the processor cannot determine if the sensor is detecting Sector B or D. However, after the state change to dark and the count of twenty-two steps, plus two steps to allow for sector edge tolerance uncertainty, the processor assigns the position as step one-hundred and seventeen because Sector A has only twenty-one steps of dark.

Path E begins in Sector C just after Sector B. After the processor counts twenty-two continuous steps of dark, plus two steps to allow for sector edge tolerance placement uncertainty, it knows that the sensor is detecting Sector C; however, it does not know where in the sector it is and must wait for the state change to obtain a positive step position of step zero.

In Path F, the sensor starts up in Sector C at a point having twenty one, plus two steps to allow for sector edge tolerance uncertainty, or fewer dark steps remaining. The processor must then wait until twenty-six light steps, plus two steps to allow for sector edge tolerance uncertainty, have been counted to confirm that the sensor is at step twenty eight.

Finally, Path G is similar to Path E in that the processor determines that the sensor is in Sector C after twenty-two steps, plus two steps to allow for sector edge tolerance uncertainty, but must wait until the state change from dark-to-light to obtain a precise position. This path determines the maximum negative volume that may be pumped before synchronization.

In one embodiment, the paths had the following numbers of steps taken and the following amounts of fluid pumped before position determination was accomplished:

| Path | Steps Taken | Volume Pumped (µl) |
| --- | --- | --- |
| A | 47 | 73.97 |
| B | 48 | 71.07 |
| C | 46 | 67.92 |
| D | 48 | 50.25 |
| E | 107 | 30.80 |
| F | 51 | 64.88 |
| G | 82 | 15.10 |

Even though Path E took one-hundred and seven steps before the position was determined, only 30.8 µl were pumped. This is because a negative volume area 98 was encompassed by this path and lowered the net amount pumped.

As mentioned above, sequential step volumes vary. Some sequences of pump steps pump more volume than others. This is graphically illustrated and described above. Path A included only forty-seven steps but pumped 73.97 µl while Path E included many more steps but pumped less than half the amount. In the embodiment shown, the position disk 24 has been positioned to have the sequential step positions corresponding to a low flow period positioned within the large or second opaque sector 29. Because the second opaque sector has the characteristic of requiring the greatest number of motor steps turned before the step position can be determined, it is desirable to have the least volume of fluid pumped during this large number of steps.

On the other hand, the position disk 24 has been positioned so that the sequential step positions corresponding to a high flow period are positioned within the small or first opaque sector 28. However, in these sectors, the least number of motor steps are turned before the disk position is determined. The greatest volume of fluid will be pumped during this period but the disk's position will be more quickly ascertained.

Figures 6, 7:
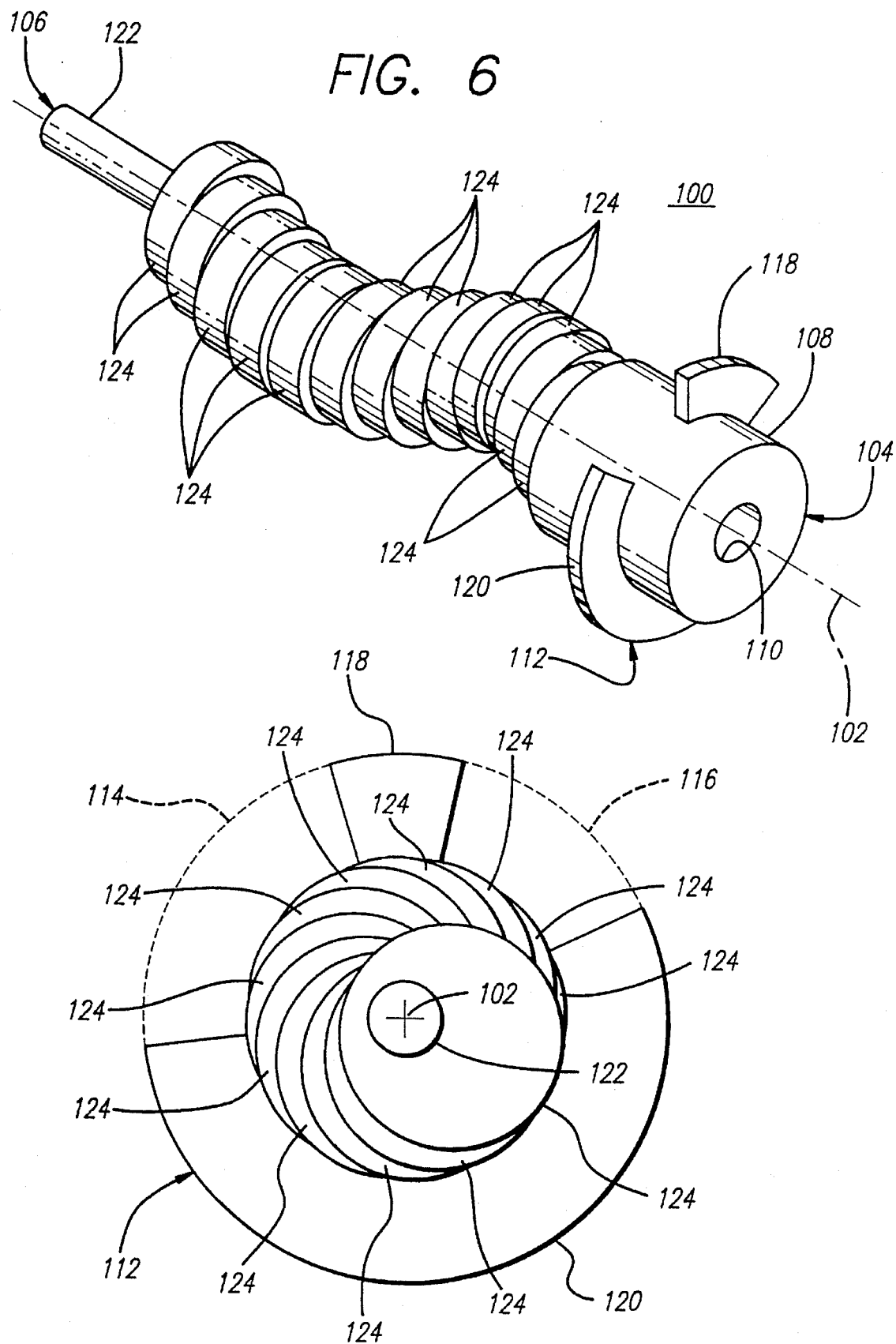
FIG. 6 is a perspective view of one embodiment of an aspect of the invention showing a positioning disk, similar to that shown in FIG. 2, integrally formed with the pump shaft and cams of a peristaltic fluid delivery system.
FIG. 7 is an enlarged end view of the positioning disk, pump shaft and cams shown in FIG. 6.

Referring now to FIGS. 6 and 7, the camshaft 122, cams 124, and position disk 112 have all been integrally formed as one piece and that piece is referred to as the "drive member." With particular reference to FIG. 6, the camshaft member is elongated and formed generally about a central longitudinal axis 102, the camshaft member having first 104 and second 106 ends. The second end 106 of the camshaft member is reduced in diameter 122 for mounting as described below. The first end includes an enlarged diameter cylindrical hub 108 formed with an axial bore 110 therein extending from the first end inwardly to terminate within the hub a predetermined axial distance to receive the output shaft of the motor 19.

The position disk 112 in this embodiment also includes a plurality of slots in the disk to form markers for position determination by a single photo-electric sensor, as in the example previously described. The two slots 114 and 116 correspond to the two transparent sectors described above and the two sectors of remaining material 118 and 120 of the disk correspond to the opaque sectors described above.

The camshaft member 100 shown has been formed of a plastic material, such as an opaque Teflon®-filled polycarbonate plastic, and may be formed by injection molding processes well known to those skilled in the art. By using this material, the cams have low frictional properties so that the pinching fingers or cam followers slide easily over the cams while the opaque characteristic of the material operates in the opaque sectors 118 and 120 of the position disk 112 to block the transmission of light to the photo detector of the optical sensing device.

It has also been found that improved performance results when the injection mold used in the process is constructed so that the break lines or separation lines caused by the separation of the mold halves are positioned at non-critical locations on the cam surfaces. In the embodiment shown, the break lines were located on the side surfaces of each of the cams between the least or greatest radial offset points from the center of rotation, and not at the top dead center or bottom dead center points. Thus the fingers interacting with the cams will not experience the greatest forces at a separation line and this reduces wear in the respective components. In addition, any forming flaws or non-uniformities, such as surface sinking at or near the separation line is not located on the critical surfaces of the cam.

It can be appreciated that the integrally formed drive member having the cams and position disk formed as one piece can alleviate manufacturing difficulties that would be associated with attempting to press fit a plurality of cams and the position disk in correct alignment on a cam shaft. Also, injection molding a plastic drive member results in less expense in forming the drive member than if it were machined from brass or other material. Furthermore, the injection molding process can produce a large quantity of like units at a considerably reduced cost.

When installed in a peristaltic pumping mechanism, the drive shaft 122 of the camshaft member 100 is fit into a bushing contained in the pump housing so that the second end 106 of the camshaft member 100 is free to rotate. The output shaft of the motor is press fit into the hub bore 110 of the shaft, the camshaft member being rotated by the motor as it is controlled by the microprocessor. Because the position disk is molded with the cams, accuracy is increased. The position of the motor shaft when pressed into the hub of the drive member is not critical as the position disk provides information about the positions of the cams. Therefore, as long as the optical sensors are mounted consistently in relation to position disks and the drive members are pressed onto motor shafts without rotating the motor shaft out of a rest position, consistent results can be obtained when manufacturing large numbers of the drive system.

The size of the transparent and opaque sectors are not limited to the disk illustrated and described above and referred to in FIGS. 2 through 5. Sectors corresponding to more or fewer step increments can be used depending on the limitation on the maximum quantity of fluid that can be pumped before the drive member position is determined. In addition, a different number of alternating transparent and opaque sectors may be used to provide motor drive member rotational position. However, a position disk having only two transparent and two opaque sectors and a single optical sensor for sensing the disk has been found to reduce system hardware and software complexity, in turn lowering manufacturing costs. Because of the fewer number of parts and reduced complexity, the reliability of the system is increased.

It will be apparent from the foregoing that the system of the invention is capable of quickly, accurately, and efficiently determining the position of a drive member within a limited number of steps turned by the drive member with a reduced amount of hardware and lowered manufacturing costs.

While particular forms of the invention have been illustrated and described, various modification can be made without departing from the spirit and scope of the invention. Accordingly, it is not intended that the invention be limited, except as by the appended claims.

What is claimed is:

1. A system for determining the position of a drive member, the drive member moving in a plurality of movement increments over a complete rotation, the drive member connected to a pumping mechanism such that as the drive member turns through the plurality of movement increments over the complete rotation, the pumping mechanism correspondingly pumps volume increments of fluid, at least some of the volume increments varying in quantity from other volume increments, the system comprising:

a disk coupled to the drive member for rotation therewith, the disk having a plurality of spaced-apart markers, the number of markers being less than the plurality of movement increments of the drive member, the positions of the markers on the disk selected such that the markers are located on the disk in known positions that correspond to particular volume increments pumped by the pumping mechanism and the spacing between the markers selected so that known volume totals are pumped by the pumping mechanism between said markers with the markers being located closer together to correspond to higher pumped volume increments and the markers being located farther apart to correspond to lower pumped volume increments;

a sensor located to sense the markers of the disk as the drive member rotates and to produce marker signals upon sensing the markers; and a processor that provides control signals to cause the drive member to turn sequentially through the plurality of movement increments, the processor receiving the marker signals from the sensor and counting the movement increments of the drive member between receipt of marker signals to calculate the position of the drive member based on the receipt of marker signals and the number of movement increments counted.

2. A system according to claim 1 wherein the markers are of different sizes and the sizes of the spaces between the markers are also different.

3. A system according to claim 1 wherein the sizes of the markers are selected to correspond to different pluralities of volume increments and the sizes of the spaces located between the markers are selected to be different from each other and from the sizes of the markers with smaller sized markers and smaller sized spaces located to correspond to volume increments of the pumping mechanism in which larger volumes are pumped and with larger sized markers and larger sized spaces located to correspond to volume increments of the pumping mechanism in which smaller volumes are pumped, so that the processor in counting the number of movement increments between markers and spaces can determine the position of the drive member in less than one complete rotation while reducing the amount of fluid pumped in making said position determination.

4. A system according to claim 1 wherein the sensor is an optical sensor, and the disk has a plurality of transparent and opaque sectors to form the markers.

5. A system according to claim 4 wherein the transparent sectors have different sizes and two opaque sectors are separated and alternate with the transparent sectors wherein the sizes of the opaque sectors are selected to correspond to different pluralities of volume increments and the sizes of the transparent sectors located between the opaques sectors are selected to be different from each other and from the opaque sectors with smaller sized opaque sectors and smaller sized transparent sectors located to correspond to volume increments of the pumping mechanism in which larger volumes are pumped and with larger sized opaque sectors and larger sized transparent sectors located to correspond to volume increments of the pumping mechanism in which smaller volumes are pumped, so that the processor in counting the number of movement increments between opaque sectors and transparent sectors can determine the position of the drive member in less than one complete rotation while reducing the amount of fluid pumped in making said position determination.

6. A system according to claim 5 wherein the drive member comprises a stepper motor and the processor controls the stepper motor to rotate in the incremental movements over the complete rotation.

7. A system according to claim 5 wherein the spaces between markers are formed of sectors having different angular sizes with one such sector being larger than the other sectors, the larger sector positioned on the disk corresponding to a group of smaller volume increments pumped by the pumping mechanism.

8. A system for determining the position of a drive member of an infusion pump, the drive member being driven by a stepper motor rotating the drive member, the drive member moving in a plurality of movement increments over a complete rotation, the drive member connected to a pumping mechanism such that as the drive member turns through the plurality of movement increments over a complete rotation, the pumping mechanism correspondingly pumps volume increments of fluid, at least some of the volume increments varying in quantity from other volume increments, the system comprising:

a disk coupled to the drive member for rotation therewith, the disk having a plurality of first sectors and a plurality of second sectors alternating with the first sectors, the number of sectors being less than the plurality of movement increments of the drive member, the positions of the sectors on the disk selected such that the sectors are located on the disk in known positions that correspond to particular volume increments pumped by the pumping mechanism and the sizes of the sectors selected so that known volume totals are pumped by the pumping mechanism during each sector with the sectors being smaller to correspond to higher pumped volume increments and the sectors being larger to correspond to lower pumped volume increments wherein the positions and sizes of the sectors are selected so that locating the position of the drive member from any position on the disk results in pumping of a reduced volume of fluid by the pumping mechanism;

a sensor located to sense the sectors as the drive member rotates and to produce a first position signal at each movement increment corresponding to a first sector and a second position signal at each movement increment corresponding to a second sector; and a processor that provides control signals to cause the motor to turn the drive member sequentially through the plurality of movement increments, and to receive multiple position signals from the sensor and to count the movement increments turned while receiving first and second position signals and to calculate the position of the drive member based on the number and type of movement increments counted.

9. A system according to claim 8 wherein the first and second sectors are of different angular sizes.

10. A system according to claim 8 wherein the first sectors comprises opaque sectors and the second sectors comprise transparent sectors.

11. A system according to claim 10 wherein the sizes and placement of the opaque and transparent sectors are selected so that the drive member rotates no more than a certain number of movement increments before its position is calculated.

12. A system according to claim 8 wherein the second sectors comprise transparent sectors that are formed as two apertures in the disk.

13. A system for determining the position of a drive member of an infusion pump, the drive member being driven by a stepper motor rotating the drive member, the drive member moving in a plurality of movement increments over a complete rotation, the drive member connected to a pumping mechanism such that as the drive member turns through the plurality of movement increments over a complete rotation, the pumping mechanism correspondingly pumps volume increments of fluid, at least some of the volume increments varying in quantity from other volume increments, the system comprising:

a disk coupled to the drive member for rotation therewith, the disk having a plurality of opaque sectors and a plurality of transparent sectors alternating with the opaque sectors, the number of sectors being less than the plurality of movement increments of the drive member, the positions of the sectors on the disk selected such that the sectors are located on the disk in known positions that correspond to particular volume increments pumped by the pumping mechanism and the sizes of the sectors are selected so that known volume totals are pumped by the pumping mechanism during each sector with the sectors being smaller to correspond to higher pumped volume increments and the sectors being larger to correspond to lower pumped volume increments wherein the positions and sizes of the sectors are selected so that locating the position of the drive member from any position on the disk results in pumping of a reduced volume of fluid by the pumping mechanism;

an optical sensor located to sense the sectors as the drive member rotates and to produce a first position signal at each movement increment corresponding to an opaque sector and a second position signal at each movement increment corresponding to a transparent sector; and a processor that provides control signals to cause the motor to turn the drive member sequentially through the plurality of movement increments, and to receive position signals from the sensor and to count the movement increments turned while receiving the first and second position signals to determine the position of the drive member thereby.

14. The system of claim 13 wherein each transparent sector has a different angular size from each other transparent sector and from each opaque sector and each opaque sector has a different angular size from each other opaque sector.

* * * * *